United States Patent
Singh et al.

[11] Patent Number: 5,560,960
[45] Date of Patent: Oct. 1, 1996

[54] POLYMERIZED PHOSPHOLIPID MEMBRANE MEDIATED SYNTHESIS OF METAL NANOPARTICLES

[75] Inventors: Alok Singh, Sprungfield, Va.; Gan-Moog Chow, Bowie, Md.; Michael Markowitz, Burke, Va.

[73] Assignee: The United States of America as represented by the Secretary of the Navy, Washington, D.C.

[21] Appl. No.: 334,130

[22] Filed: Nov. 4, 1994

[51] Int. Cl.⁶ ....................................................... B05D 7/00
[52] U.S. Cl. ................ 427/222; 427/301; 427/304; 427/305; 427/306; 427/443.1
[58] Field of Search ................ 427/222, 443.1, 427/301, 304, 305, 306

[56] References Cited

U.S. PATENT DOCUMENTS 4,911,981  3/1990  Schnur et al. ................ 428/371

OTHER PUBLICATIONS

Markowitz et al., "Palladium Ion Assisted Formation and Metallization of Lipid Tubules"., Thin Solid Films 224 (1993) pp. 242–247.

Chow et al., *JOM*, vol. 45, No. 11 (Nov. 1993).

Markowitz et al., B *Langmuir* (1994) (8 pages) (no month).

*Primary Examiner*—Shrive Beck
*Assistant Examiner*—David M. Maiorana
*Attorney, Agent, or Firm*—Thomas E. McDonnell; Barry A. Edelberg

[57] ABSTRACT

Nanoparticle metal powder having a controllable and narrow size distribution are by electrolessly plating a metal on the interior of a vesicle made of at least one polymerized phospholipid. Electroless plating may be accomplished by catalytic reduction of the metal ion or u.v. reduction of the metal ion.

10 Claims, 1 Drawing Sheet

STEPS INVOLVED IN METALLIZATION

LIPID MIXTURE HYDRATION → VESICLE FORMATION → POLYMERIZATION

→ PALLADIUM BINDING DIALYSIS → METALLIZATION → CHARACTERIZATION

POLYMERIZED PHOSPHOLIPID MEMBRANE MEDIATED SYNTHESIS OF METAL NANOPARTICLES

BACKGROUND OF THE INVENTION

1. Field of the Invention

The present invention relates generally to nanometer-sized particles and in particular to nanometer-sized metal particles.

2. Description of the Background Art

Because of their size (1–100 nm) nanoparticles exhibit surface and volume effects not observed for larger dimension particles. As a result, it is believed that nanoparticles may have unique optical, dielectric, magnetic, mechanical, and transport properties which would find use in many types of applications such as catalysis, sensors, optics, ceramics and metallurgy. In order to be useful building blocks for new types of materials, it is desirable that nanoparticles have a high degree of purity, a narrow size distribution and chemical stability and should remain monodispersed during formation and processing into materials. The formation of well dispersed suspensions of nanoparticles is a particularly difficult challenge since particles of this size irreversibly agglomerate in order to minimize their high interfacial energy.

Conventionally, a number of approaches have been taken to synthesize nanoscale particles such as the vapor phase method, mechanical milling, and solution chemistry. Both vapor phase synthesis and mechanical milling produce agglomerated nanoparticles. Ceramic hydroxides, metals of group 6–11 elements, ferrofluids of amorphous iron as well as other nanoparticles have been synthesized using solution chemistry in the presence of surfactants in order to prevent agglomeration. Recently, some research efforts have been focussed on using vesicles as reaction cages to do solution chemistry with an aim to produce well-dispersed particles with a narrow size distribution. In addition, exterior vesicle surfaces have been decorated or coated with Ni, CdS, and ZnS. The vesicles coated on the exterior surface tend to agglomerate while particles formed with in vesicles remained dispersed. This approach suffers man, drawbacks such as disintegration of the vesicle, poor yield of the precipitated materials, lack of purity of the powders produced and difficulties in reproducibly processing these materials. In addition, the stability of the membranes to the chemical and physical stress that occurs during the synthesis and the processing of the nanoparticles demands a thorough investigation.

SUMMARY OF THE INVENTION

It is an object of the present invent ion to form nanometer-sized metal particles having a narrow size distribution.

It is another object of the present invention to form nanometer-sized metal particles of a controlled size.

It is a further object of the present invention to provide nanometer-sized metal particles that remain monodispersed during formation and processing into other materials.

These and other goals are accomplished by precipitating nanometer-sized metal particles from solution within vesicles made from polymerizable phospholipids. Polymerized phospholipid vesicles of a desired size are formed and added to an electroless plating bath for the metal to be formed into nanoparticles. The electroless plating bath diffuses through the lipid bilayers into the vesicles. The kinetics of this diffusion may be controlled by the nature and degree of cross-linking. Upon appropriate treatment with a catalyst or u.v. radiation, the desired metal forms nanometer sized particles inside the vesicle. The resulting metallized vesicles may then be used in the preparation of advanced materials which require dispersed nanoscale particles with small size distribution.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
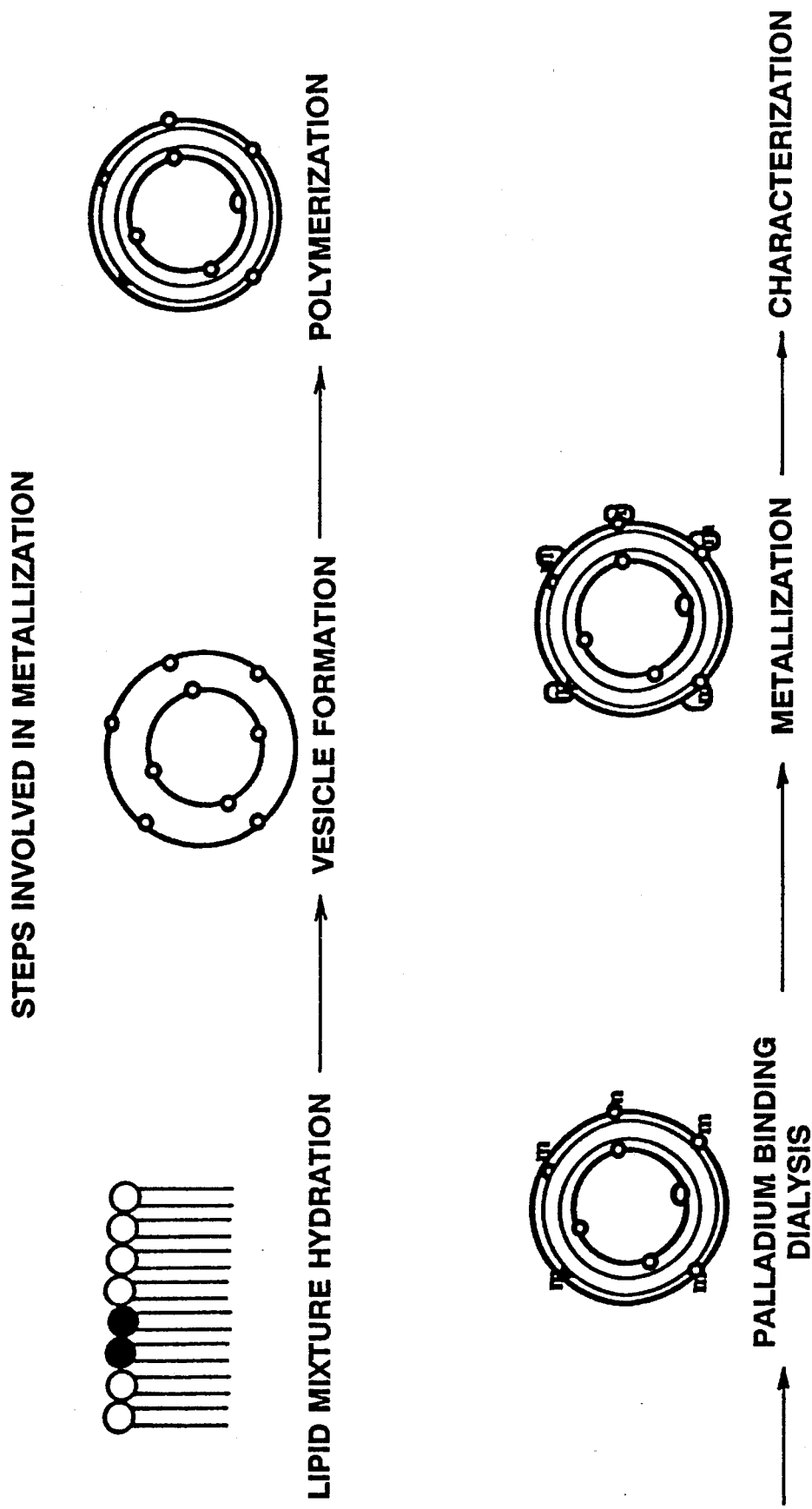
FIG. 1 is a schematic flowchart illustrating the hydration, formation, polymerization, catalyst binding, metallization and characterization of a vesicle having a lipid bilayer structure.

The overall method of the present invention is outlined in FIG. 1. As shown there, the vesicles are formed by conventional means from a hydrated phospholipid, and more typically from a hydrated mixture of phospholipids. The vesicles are then polymerized. If the nanoparticle powder is other than a noble metal, a catalytic metal is bound to the polymerized vesicles by diffusion of a catalytic salt of the desired metal into the polymerized or unpolymerized vesicles (although polymerization is simpler if the catalytic metal salt is present before polymerization), or a catalytic metal salt may be present during the initial formation of the vesicles. Then, the vesicles are metallized with the desired metal. As shown in FIG. 1, metallization proceeds on the interior and exterior surfaces of the polymerized vesicles if the catalyst is not removed from the exterior surface of the polymerized vesicles. (To favor the formation of nanoparticles of a controlled size, and to reduce agglomeration, it is most often desirable to prevent metallization on the exterior surfaces of the polymerized vesicles). The metallized polymerized vesicles may then characterized.

The polymerized phospholipid vesicles used in the method of the present invention are formed by the polymerization of vesicles formed from polymerizable phospholipids. To be useful in the preparation of nanometer-scale particles, the vesicles must be small, typically on the order of less than about 1200Å. Usually, the vesicles are 20 nm or greater in diameters. Any phospholipid bearing crosslinking groups may be used. For example, phospholipids having diacetylene, diene, methacrylate, styryl, lipoic acid or thiol groups can be employed. To best protect the polymerized vesicles from rupture, all phospholipids used to form the vesicles should be polymerizable.

Typically, more than one polymerizable phospholipid is employed. To avoid unneeded expense, however, all polymerizable phospholipids in the mixture usually have the same crosslinkable functionalities. The following is a partial listing of polymerizable phospholipids that may be use in the method of the present invention.

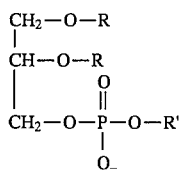

1. R = OC(CH$_2$)$_8$—C≡C—C≡C—(CH$_2$)$_9$—CH$_3$;
   R' = CH$_2$—CH$_2$—NMe$_3$ (Charge neutral)

2. R = OC(CH$_2$)$_8$—C≡C—C≡C—(CH$_2$)$_9$—CH$_3$;
   R' = CH$_2$—CH$_2$—OH

3. R = OC(CH$_2$)$_8$—C≡C—C≡C—(CH$_2$)$_9$—CH$_3$;
   R' = CH$_2$—CH$_2$—CH$_2$—OH

4. R = OC(CH$_2$)$_8$—C≡C—C≡C—(CH$_2$)$_9$—CH$_3$;
   R' = H

An aqueous suspension containing the polymerizable phospholipids is then subjected to any procedure used for the formation of bilayer phospholipid vesicles. Procedures for forming bilayer phospholipid vesicles are well-known in the art, and will thus not be described here. For example, a lipid bilayer vesicle may be formed by extrusion or sonication. Sonication may be the preferred method, since it reliably provides vesicles of small uniform and controllable size. Bilayer vesicles typically have diameters of about 30 nm to about 60 nm. Bilayer vesicles having diameters within that range are of a size useful in the present invention. Generally, vesicles having two bilayers are preferred over vesicles having multiple bilayers, and vesicles having a single bilayer are most preferred. This preference arises because diffusion is more efficient across a single bilayer membrane. Diffusion into the vesicle is an essential step for making particles inside the vesicle cavity.

After this initial formation step, the vesicle is then polymerized to enhance its stability. The vesicles may be polymerized by any means used for the cross-linking polymerization of lipid vesicles having the functional present on the polymerizable lipids. Typically, the vesicles are polymerized by exposure to u.v. radiation for a time sufficient to permit the completion of cross-linking. Typically, a wavelength of 254 nm is used. Incomplete cross-linking might leave the vesicles too fragile for facile handing.

Electroless deposition of metals generally requires the use of a catalyst, such as a water-soluble palladium salt or other water-soluble salt of a catalytic metal (e.g. platinum salt). To permit the deposition of metals on the of the vesicles, the catalytic metal salt is best added to the dispersing medium before vesicle formation, since there is no concern with damage to vesicles at that time. Another preferred is to prebind the catalytic metal ion to the negatively charge phospholipids before vesicle formation, which also avoid concerns over damaging vesicles. Any catalytic metal salt on the exterior of the vesicles is removed after polymerization of the vehicles to ensure that metal nanoparticles form only on the inside of the vesicles. Typically, the catalytic metal salt is removed by exposing the exterior surface of the vesicle to a chelating agent, such as ethylenediaminetetraacetic acid (EDTA), and gel filtering the suspension of vesicles. Alternatively, the vesicles can be passed through an ion exchange column to remove the externally bound Pd$^{2+}$ ion. Failure to remove essentially all catalytic material from the exterior surface of the vesicle leads to undesirable agglomeriation and may prevent complete formation of inside the vesicle.

When a catalyst for electroless deposit is used, negatively charged polymerizable phospholipids along vesicular membrane serve as binding sites for the catalytic metal. Thus, where a catalytic metal salt is employed, the phospholipids from which the vesicle is polymerized should include a sufficient concentration of charged phospholipid to bind at least an amount of catalyst metal that significantly enhances the rate of electroless deposition of the desired metal within the polymerized vesicle. Assuming a 1:1 correspondence between available catalytic metal and catalytic binding sites along the negatively charged phospholipids (which is usually the case), up to about 50 weight percent of the total amount of polymerized phospholipids in the vesicle are negatively charged. The remainder of the polymerized phospholipids in the vesicle are usually charge neutral. If more than 50 weight percent of the total amount of polymerized phospholipids in the vesicle are negatively charged (assuming a 1:1 correspondence between available catalytic metal and catalytic binding along the negatively charged phospholipids), it may be more difficult, although not impossible, to form vesicles. Additionally, an overabundance of catalyst within a vesicle can increase particle size or interfere with the growth of particles of some metals on the other hand, if the vesicles include too few negatively charged polymerized phospholipids (more than one weight percent, and usually at least about weight percent is most often used), then the vesicle membrane will bind an insufficient amount of catalyst to significantly promote the electroless deposition of the desired metal.

Once the polymerized vesicle has formed, and any catalyst bound to the outside surface of the vesicle has been removed, the polymerized vesicles are suspended in a protic (typically aqueous) solution for the electroless deposition of the desired metal. Any protic solution used for electroless deposition of the desired metal may be used. Typically, solutions used for electroless deposition include at least one metal ion and a reducing agent. Typically reducing agents useful in the present invention include, but are not limited to, tannic acid, ascorbic acid, hypophosphite, dimethylamineborane (DMAB) and formaldehyde. The required diffusion of the metal ion and reducing agent into the interior of the vesicle may be accelerated by mixing, for example, by stirring or sonication in any common laboratory sonnicating bath cleaner, at low power. The power applied during mixing, whether by sonication or stirring, should not be so great as to rupture the polymerized vesicles. The appropriate amount of power to be applied may be empirically determined without undue experimentation. Once the desired metal ion and the reducing agent diffuse into the vesicle, the reducing agent reduces the catalytic metal salt and the electroless plating of the desired metal begins. Typically, the electroless plating process is completed in about one to about three hours, although the reaction may be faster or slower in some circumstances. The speed of reaction depends on the nature of the reducing agent, temperature and other reaction conditions. Typically, the reaction is performed at about 15° C. to about 50° C. During electroless plating, the metal ions are reduced to metals, for example, by hydrogenation.

Nanoparticles of noble metals are produced by essentially the same procedure used to make nanoparticles of other metals, although it may be accomplished without a catalytic metal salt. When no catalyst is used and the desired metal cat ion has fully diffused into the vesicle, the vesicles are placed in a u.v. reactor, typically at 254 nm, for about three hours or until the u.v. completely reduces substantially all of the desired metal ion. If desired, a radical scavenger may be diffused into the vesicle, preferably after polymerization (in those case where the vesicles might otherwise be soluble in the scavenger (isopropanol, acetone) and before the plating process begins.

The size of the metal particles produced by the process of the present invention is controlled predominantly by the size of the polymerized vesicles. The size of the polymerized vesicles may be controlled by methods well-known in the art of phospholipid vesicles.

The number of metal particles per vesicle depends of the number of nucleation sites per vesicle and appears to be independent of the method employed. A ring of many small particles may form inside the vesicle when the vesicle includes many nucleation sites, or only a few larger particles may grow within the vesicle.

Nanoparticles of any metal that can be electrolessly deposited may be made according to the method of the present invention. These metals include, but are not limited to gold, silver, copper, cobalt, nickel, iron and zinc.

Having described the invention, the following examples are given to illustrate specific applications of the invention including the best mode now known to perform the invention. These specific examples are not intended to limit the scope of the invention described in this application.

EXAMPLES

Section I

Materials and Methods 1,2-Bis(tricosa-10,12-diynoyl)-sn-glycero-3-phosphohydroxyethanol and 1,2-bis(tricosa-10,12-diynoyl)-sn-glycero-3-phosphocholine were synthesized according to the procedures described in Singh, A. J. Res. 1990, 31, 1522; Singh et al., Synth Commun. 1986, 16, 847; and Singh et al., Synth Commun. 1992, 22, 2293, all of which are entirely incorporated by reference herein. $Pd(NH_3)_4Cl_2$ catalyst solution was prepared as described in Markowitz et al, Thin Solid Films, 1993, 224, 242, the entirety of which is incorporated herein by reference. The hydrodynamic radius of the particles formed was determined by light scattering (Coulter Submicron Particle Analyzer, N4MD) and the extent of monomer reaction after exposure to UV radiation was by phosphate analysis of the thin layer chromatograph, vesicles using the procedures well known in the art of analytical chemistry.

Samples, mounted on carbon or formvar coated copper grids, were examined by transmission microscopy (TEM). Crystallographic information was obtained using selected area electron diffraction technique.

Vesicle Preparation

A thin film of the lipid mixture was hydrated at 70° C. in water 30 min in the presence or absence of $(NH_3)_4Cl_2$. The total concentration of lipid in each sample rang from 2 mg/mL to 20 mg/mL. In those samples in which the palladium salt was present during vesicle formation, the concentration of $Pd(NH_3)_4Cl_2$ was equimolar to the negatively charged lipid (2). The mixture was vortexed and then sonicated (Branson sonifier, Model 450) at 60° C. for 5 min. The dispersion was then allowed to cool to room temperature and then, polymerized. Polymerization of the liposomes was accomplished by exposure to UV (254 nm, Rayonet Photochemical Reactor) at a controlled t between 8° C. through 20° until the extent of polymeriation is maximized. Then, an amount of EDTA (tetrasodium salt) equimolar to the amount of $Pd(NH_3)_4Cl_2$ present was added and then vesicles were then immediately gel filtered.

Metal Particle Formation

Metal particle deposition or formation of vesicles was accomplished with a Au or Co plating bath. The gold plating bath contained chloroauric acid and sodium hypophosphite as major components while the Co bath contained $CoCl_2$ and $(CH_3)_2N-BH_3$ as the major components (Markowitz et al, Thin Films, 1993, 224, 242 The liposomal dispersions (2 mL) were diluted with an equal volume of the plating bath. In the case of metal particle formation inside polymerized vesicles, plating was allowed to continue until particle formation was complete (about thirty minutes to about three hours).

Results (From Section I)

The hydrodynamic radii of the vesicles were determined by light scattering studies after the vesicles prepared from mixtures of 1 and 2 had been exposed to UV radiation (254 nm). The diameters of vesicles containing 10% of 2 (w/w) in the absence (pH 5.5) and presence of $Pd(NH_3)_4Cl_2$ (pH 9.5) did not vary greatly. In both cases, bimodal populations of vesicles were observed. In the case of the vesicles formed in the absence of palladium ion, the populations had diameters of 34.1±15 nm 101±38 nm while the diameters of vesicles formed in the presence, of palladium ion were 31±13 nm and 114±40 nm. Increasing fraction of 2 to 50% (w/w) also did not have much effect on diameters of vesicles formed in the presence of the palladium ion. As with the other preparations, a bimodal population of vesicles was formed which had diameters of 37.5±13 nm and 109±41 nm.

In order to form unagglomerated nanoparticles, the polymerized vesicles were used as reaction vials for the nanoparticle synthesis. Vesicles in the presence of $Pd(NH_3)_4Cl_2$ and containing 10% or 50% of 2 were stabilized by exposure to UV radiation. Palladium ions were removed from the external vesicle surface by addition of EDTA (tetrasodium salt) followed immediately by gel filtration. After addition of the plating bath, the resulting solution was allowed to stand for thirty minutes to six hours. Transmission electron micrographs of gold nanoparticles formed within the large polymerized vesicles containing 10% of 2 were also made. The particle size ranged from 40 –100 nm. The electron diffraction rings that arose from a mixture of gold and impurities which were probably due to unreacted precursors. Bright field imaging of particles formed inside small diameter vesicles indicated that nanoscale particles were formed inside the membrane of polymerized vesicles containing 50% of 2 (w/w). The particles were found to be in the range of 4 to 15 nm. The diffraction ring was identified to be Au.

Transmission electron micrographs of mixture of cobalt and cobalt hydroxide particles produced inside vesicles containing 50% of 2 (w/w) after bath sonication for 2.5 hrs were made. Analysis of the diffraction rings suggested the formation of a mixture of cobalt and cobalt hydroxides $(Co(OH)_2)$. Selected area electron diffraction performed on individual vesicles showed many vesicles contained single crystals.

Section II

Materials Used 1,2-Bis(tricosa-10,12-diynoyl)-sn-glycero-3-phosphocholine (1)

1,2-Bis(tricosa-10,12-diynoyl)-sn-glycero-3-phosphohydroxyethanol (2)

1,2-bis(tricosa-10,12-diynoyl)-sn-glycero-3-phosphohydroxypropanol (3)

1,2-bis(tricosa-10,12-diynoyl)-sn-glycero-3-phosphatidic acid (4)

1,2-bis(palmitoyl)-sn-glycerol-3-phosphohydroxyethanol (5)

1,2-dialkyl-sn-glycero-3-phosphohydroxyethanol (from soy lecithin) (6)

Phopsholipids 2–6 were prepared from the corresponding phosphocholines by the phospholipase D catalyzed transphosphatidylation procedure (Singh et al., *Synth Commun.* 1992, 22, 2293). $Pd(NH_3)_4Cl_2$ catalyst solution was prepared as described in Markowitz et al, *Thin Solid Films,* 1993, 224 242, the entirety of which is incorporated herein by reference. A 0.2 M aq. acetate buffer (pH 5.6) and triple distilled water were used as dispersion/reaction medium.

General Method for Microstructure Preparation
Preparation of Vesicles

A vacuum dried, thin film of the phospholipid mixture was hydrated at 60° C. in water or 0.2 M aq. acetate buffer (pH 5.6) for 30 min. The total concentration of phospholipid in each sample was 2 mg/mL. The mixture was vortexed and then sonicated (jacketed cup horn Branson sonifier, model 450) at 60° C. for 5 min to ensure complete dispersion. The dispersion was then allowed to cool to room temperature. The vesicles were then exposed to UV radiation (254 nm, Rayonet Photochemical Reactor) at 8° C. for 15 min. Then, 20 μL of a 50 mM aq. $Pd(NH_3)_4Cl_2$ solution in water was added. After 5 min the dispersions were dialyzed against water to remove buffer salt and excess $Pd(NH_3)_4Cl_2$. The size of the vesicles formed was determined by light scattering (Coulter Submicron Particle Analyzer, N4MD Metallization Process Metallization wit a Ni plating bath is carried out following a previously described process. Vesicles were also metallized with a Au plating bath containing chloroauric acid and sodium hypophosphite as major components. To both polymerized and unpolymerized liposome dispersions (2 mL) an equal volume of the Au plating bath was added. Plating was allowed to continue for 30 min to 2 hrs. The dispersions were then dialyzed against water (5 L) for 3 hrs to remove excess plating bath leaving metallized vesicles. Metallized vesicles were examined by microscopic techniques for metal growth.

Characterization of Vesicles and Metallized Particles

Vesicle size was monitored by light scattering technique. Vesicles after metal deposition or polymerization were also visualized using transmission electron microscopy.

For metal characterization selective area electron diffraction was performed using the transmission electron microscope. From the measurements of the diffracting rings, the corresponding d spacings were calculated and the crystal structure determined using the ratio tests of the (hkl) values.

SPECIFIC EXAMPLES FOR SECTION II

Example 1

To Demonstrate the Passivity of Phosphochcoline Headgroup Towards Metallization Process One milliliter dispersion (concentration 2 mg/mL) obtained by hydrating thin film of 1 at 60° C. in either water or 0.2 M aq. acetate buffer (pH 5.6) for 30 minutes followed by vortex mixing and sonication (Branson Cup sonifier) at 60° C. for 5 min. was polymerized by exposing to UV radiation (254 nm, Rayonet Photochemical Reactor) at 8° C. for 15 min . To the polymerized dispersion, 20 μL of a 50 mM aq. $Pd(NH_3)_4Cl_2$ solution was added. After 5 minutes, the dispersion was dialyzed against water to remove buffer salt and excess $Pd(NH_3)_4Cl_2$. The vesicles were diluted with an equal volume of the Au plating bath. Plating was allowed to continue for 30 min to 2 hrs. The dispersions were then dialyzed against water (5 L) for 3 hrs to remove excess plating bath and the vesicles were examined by TEM No electroless metal plating of the vesicles was observed. This is example is evidence that charge neutral lipids or surfactants will not serve as nucleation sites for the electroless metal plating of microstructures using this method.

Example 2

Metallization of Mixed Lipid Vesicles in 9:1, w/w) A thin film of a 9:1 mixture of phospholipids 1 and 2 (phosphohydroxyethanol headgroup) was hydrated at 60° C. in either water or 0.2 M aq. acetate buffer (pH 5.6) for 30 min. The total concentration of lipid in each sample was 2 mg/mL. The mixture was vortex mixed and then sonicated at 60° C. for 5 min. The dispersion was then allowed to cool to room temperature. A one mL aliquot from the dispersion was photopolymerized at 8° C. for 15 min. Then, 20 μL of a 50 mM aq. $Pd(NH_3)_4Cl_2$ solution in water was added. The diameter range of polymerized vesicles observed by TEM was 0.10 μm to 0.45 μm. After 5 min, the dispersions were dialyzed against water to remove buffer salt and excess Pd $NH_3)_4Cl_2$. The vesicles were diluted with an equal volume of the Au plating bath. Plating was allowed to continue for 30 min to 2 hrs (preferably 1 hour). The dispersions were then dialyzed against water (5 L) for 3 hrs to remove excess plating bath and the vesicle were examined by TEM. The diameters of the metallized vesicles ha e increased 2 to 4 fold over those of the nonmetallized vesicles. The metal particles deposited on the lipid surface are present as clusters of various sizes. Selected area electron diffraction of metallized vesicles of 9:1 mixture of and 2 revealed that the deposited particles on the liposome surfaces were polycrystalline. It was found that the deposits had a fcc structure by using the ratio tests of the (hkl) values. The lattice constant was determined to be 3,996 Å (known lattice constant for fcc gold is 4.0786 Å). The deposited particles on the liposome surfaces were therefore identified as fine gold particles. This example is evidence that the external surface of a polymerized vesicle containing a negatively charged lipid or surfactant with the plladium ion bound phosphohydroxyethanol headgroup can serve as the nucleation site for electroless metallization and that metal growth occurs over the surface of the vesicle.

Example 3

Metallization of Mixed Lipid Vesicles (1:2, 3:1, w/w)

A thin film of a 3:1 mixture of 1 with 2 (phosphohydroxyethanol headgroup) was hydrated at 60° C. in water or 0.2 M aq. acetate buffer (pH 5.6) for 30 min. The total concentration of lipid in each sample was 2 mg/mL. A one mL lipid/buffer mixture was vortex mixed and then sonicated at 60° C. for 5 min. The dispersion was then allowed to cool to room temperature. The vesicles were then photopolymerized at 8° C. for 15 min. Then 20 μL of a 50 mM aq. $Pd(NH_3)_4Cl_2$ solution in water was added. The diameter range of polymerized vesicles observed by TEM was 645+ −330 Å. After 5 min, the dispersions were dialyzed against water to remove buffer salt and excess $Pd(NH_3)_4Cl_2$. The vesicles were diluted with an equal volume of the Au plating bath. Plating was allowed to continue for 30 min to 2 hrs. The dispersions were then dialyzed against water (5 L) for 3 hrs to remove excess plating bath and the vesicles were examined by TEM. The diameters of the metallized vesicles have increased 2 to 4 fold over those of the no metallized vesicles.

Example 4

Metallization of Mixed Lipid Vesicles (1:3 3:1, W/w)

A thin film of a 3:1 mixture of 1 with 3 phosphohydroxypropanol headgroup) was hydrated at 60° C. in 0.2 M aq. acetate buffer (pH 5.6) for 30 min. The total concentration of lipid in each sample was 2 mg/mL. A one mL mixed lipid dispersion was vortex mixed and then sonicated at 60° C. for 5 min. The dispersion was then allowed to cool to room temperature. The vesicles were then photopolymerized at 8° C. for 15 min. Then 20 µL of a 50 mM aq. $Pd(NH_3)_4Cl_2$ solution in water was added. The diameter range of polymerized vesicles formed was observed by TEM (0.936+—470Å). After 5 min, the dispersions were dialyzed against water to remove buffer salt and excess $Pd(NH_3)_4Cl_2$. The vesicles were diluted with an equal volume of the Au plating bath. Plating was allowed to continue for 30 min to 2 hrs. The dispersions were then dialyzed against water (5 L) for 3 hrs to remove excess plating bath and the vesicles were examined by TEM. This example is evidence that the external surface of a polymerized vesicle containing a negatively charged lipid or surfactant with the palladium ion bound phosphohydroxypropanol headgroup can also serve as the nucleation site for electroless metallization and that metal growth occurs over the surface of the vesicle.

Example 5

Metallization of Mixed Lipid Vesicles (1:4, 3:1,

A thin film of a 3:1 mixture of with 4 (phosphatidic acid headgroup) was hydrated at 60° C. in 0.2 M q. acetate buffer (pH 5.6) for 30 min. The total concentration of lipid in dispersion was kept 2 mg/mL. The dispersion (1 mL) was vortex mixed and then sonicated at 60° C. for 5 min. The dispersion was then allowed to cool to room temperature. The vesicles were then photopolymerized at 8° C. for 15 min. Then, 20 µL of a 50 mM aq. $Pd(NH_3)_4Cl_2$ solution in water was added. The average diameter range of polymerized vesicles formed from 3:1 mixture of with 4 observed by light scattering was 0.117 µm+—0.063 µm. After 5 min, the dispersions were dialyzed against water to remove buffer salt and excess $Pd(NH_3)_4Cl_2$. The vesicles were diluted with an equal volume of the Au plating bath. Plating was allowed to continue for 30 min to 2 hrs. The dispersions were then dialyzed against water (5 L) for 3 hrs to remove excess plating bath and the vesicles were examined by TEM. During the process of gold plating vesicles formed from 3:1 mixtures of with 4, large particles formed which agglomerated and precipitated from solution.

Example 6

Mixed lipid vesicles (:5 or 6, 3:1 w/w)

A thin film of 3:1 mixtures of with 5 or 6 (phosphatidyl hydroxyethanol, non-polymerizable) was hydrated at 60° C. in water or 0.2 M aq. acetate buffer (pH 5.6) for 30 min. The total concentration of lipid in each sample was 2 mg/mL. The mixture was vortexed and then sonicated at 60° C. for 5 m in. The dispersion was then allowed to cool to room temperature. The vesicles were then photopolymerized at 8° C. for 15 min. Then 20 µL of a 50 mM aq. $Pd(NH_3)_4Cl_2$ solution in water was added. The average diameter of polymerized vesicles observed by light scattering was 0.28+−0.01 m and 0.0941+−0.033 m for mixture of with 6. After 5 min, the dispersions were dialyzed against water to remove buffer salt and excess $Pd(NH_3)_4Cl_2$. The vesicles were diluted with an equal volume of the Au plating bath. Plating was allowed to continue for 1 hr. The dispersions were then dialyzed against water (5 L) for 3 hrs to remove excess plating bath. During the process of gold plating vesicles only large particles formed which agglomerated and precipitated from solution. This example is evidence that the membrane must be fully polymerizable for controlled electroless plating of the surface to occur using this method.

Example 7

Metal Growth inside of Mixed lipid vesicle (1:2, 9:1 w/w):

A thin film of a 9:1 (w/w) mixture of with 2 was hydrated at 60° C. in water containing $Pd(NH_3)_4Cl_2$ in concentration equal to the concentration of the negatively charged lip id (2) for 30 min. The total concentration of lipid in each sample was 2 mg/mL. The mixture was vortexed and then sonicated at 60° C. for 5–15 min. The dispersion was then allowed to cool to room temperature. The vesicles were then polymerized at 18° C. for 15 min. Then, an amount of EDTA equal in concentration to the concentration of the $Pd(NH_3)_4Cl_2$ was added to remove $Pd(NH_3)_4^{2+}$ bound to the negatively charged lipids in the external surface of the vesicle and any excess $Pd(NH_3)_4Cl_2$. The vesicles were diluted with an equal volume plating hath containing gold salt and hypophosphite reducing agent. Plating was allowed to continue for 30 min to 6 hrs preferably thirty minutes to 3 hours. The dispersions were then dialyzed against water (5 L) for 3 hrs to remove excess plating bath and the vesicles were examined by TEM and electron diffraction. Alternatively, excess plating hath can be re moved by an addition of the chelating agent and gel filtration or by ion exchange filtration. TEM and electron diffraction revealed that gold particles had been formed inside the vesicles. This example is evidence that the internal surface of a polymerized vesicle containing a negatively charged lipid of surfactant with the palladium ion bound phosphohydroxyethanol headgroup can serve as the nucleation site for electroless metallization and that metal growth and nanoparticle formation occurs in an efficient manner using this method. The same procedure has been successfully employed on 9:1 and 3:1 mixtures of 1 and

DISCUSSION

A number of strategies exist for the stabilization of vesicles, as described in Singh et al., in *Phospholipid Handbook*; Cevc, G., Ed; Marcel Dekker: New York, 1985; pp233–291 (the entirety of which is incorporated herein by reference) and in Ringsdorf et al, *J. Angew. Chem, Int. Ed. Engl.* 1988, 27, 113 (the entirety of which is incorporated herein by reference). One of these strategies involves the covalent linking of lipids containing polymerizable groups. Vesicle stabilization may be achieved by partial polymerization through the formation of polymer domains in the membrane. As a result, channels of free volume are formed in the membrane through which cations are able to diffuse. Thus polymerized vesicles are able to be used as reaction vials for a wide range of reactions. The vesicle membrane surface can be tailored through headgroup modification of the constituent surfactants. By doing the reactions inside the polymerized vesicle, unagglomerated particles could be formed. Also, particle size, distribution, chemical homogeneity, can potentially be controlled. The results demonstrate that polymerized vesicles formed from mixtures of zwitterionic and negatively charged diacetylenic phospholipids can assist in the formation of unagglomerated nanoparticles by allowing the necessary reagents to diffuse through the membrane into the aqueous core and reacting with a catalyst which has been bound to the internal membrane surface. Vesicle membranes formed from mixtures of a palladium ion bound negatively charged lipid and a zwitterionic lipid were metallized while vesicles comprised solely of the zwitterionic lipid were not metallized. This indicates that the initial nucleation event occurs at membrane sites which have palladium ion bound to a negatively charged phospholipid headgroup. By directing the metallization process to take place within the polymerized vesicles, unagglomerated gold and cobalt/cobalt hydroxide particles were synthesized.

In addition to stabilizing vesicles polymerization provides channels for diffusion through the membrane due to the formation of randomly produced polymer domains. Non-cross linked polymerized vesicle membranes consist of many individual polymer chains and therefore contain breaks in the polymeric network which are the transport paths through the membrane. The density of these polymer "breaks" or "boundaries" depends on vesicle diameter and polymer size. In polymerized vesicles, these breaks are the main channels for transport through the membrane. Recently, the increased permeability of polymerized vesicles formed from mixtures of diacetylenic phosphocholines and sort-chain saturated phosphocholines over that of the corresponding unpolymerized vesicles has been reported. The synthesis of metal nanoparticles within the polymerized vesicles using electroless metallization chemistry indicates that these breaks act as free volume through which cations as well as anions may pass an thus greatly increase the range of reactions which could be used to prepare nanoparticles.

Further information concerning the present invention may be found in Chow et al., *JOM*, Nov. 1993, pages 62 through 65 (the entirety of which is incorporated herein by reference) and in Markowitz et al., "Polymerized Phospholipid Membrane Mediated Synthesis of Metal Nanoparticles," to be published in *Langmuir* in or near Nov. 1994 (the entirety of which is incorporated herein by reference).

Obviously, many modifications and variations of the present invention are possible in light of the above teachings. It is therefore to be understood that, within the scope of the appended claims, the invention may be practice otherwise than as specifically described.

What is claimed is:

1. A method of forming unagglomerated nanoparticles of a metal, comprising the steps of:

forming vesicles having a bilayer structure and a diameter of less than about 1200Å, each of said vesicles having a lipid component consisting essentially of at east one polymerizable lipid;

polymerizing said vesicles to form polymerized vesicles;

providing a catalytic metal salt in the interior of said polymerized vesicles before the step of diffusing said ions of said metal;

removing essentially all of any said catalytic metal salt on the outer surface of said vesicles, thus forming treated vesicles;

diffusing a solution for electroless deposition of said metal into the interior of said treated vesicles, said solution including ions of said metal;

electrolessly depositing said metal in the interior of said treated vesicles by reducing said ions of said metal.

2. The method of claim 1, wherein said solution further includes a reducing agent for reducing said ions of said metal to said metal.

3. The method of claim 1, wherein said solution includes a radical scavenger.

4. The method of claim 1, said lipid component consists essentially of a mixture of polymerizable lipids in which from more than one weight percent up to about 50 weight percent of said lipids are negatively charged, the remainder of said lipids in said mixture being charge neutral.

5. The method of claim 4 wherein said solution further includes a reducing agent for reducing said ions of said metal to said metal.

6. The method of claim 4, wherein said solution includes a radical scavenger.

7. The method of claim 4, wherein said vesicles are formed in the presence of a catalytic metal salt.

8. The method of claim 1, wherein said at least one polymerizable lipid is a phospholipid bearing cross-linkable groups selected from the group consisting diacetylene, diene, methacrylate, styryl, lipoic acid and thiol groups.

9. The method of claim 8, wherein said at least one polymerizable lipid is a diacetylenic phoapholipid.

10. The method of claim 9, wherein said diacetylenic phospholipid has the structure:

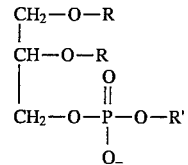

wherein R is —OC(CH$_2$)$_8$—C≡C—C≡C—(CH$_2$)$_9$—CH$_3$ and R' is —CH$_2$—CH$_2$—NMe$_3$, —CH$_2$—CH$_2$—OH, —CH$_2$—CH$_2$—CH$_2$—OH, or —H.

* * * * *